(12) United States Patent
Pierre

(10) Patent No.: US 8,181,652 B2
(45) Date of Patent: May 22, 2012

(54) INFANT POSITIVE PRESSURE TRACHEAL DEVICE

(76) Inventor: Peron B. Pierre, Brooklyn, NY (US)

( * ) Notice: Subject to any disclaimer, the term of this patent is extended or adjusted under 35 U.S.C. 154(b) by 802 days.

(21) Appl. No.: 12/264,680

(22) Filed: Nov. 4, 2008

(65) Prior Publication Data

US 2009/0288664 A1    Nov. 26, 2009

Related U.S. Application Data

(60) Provisional application No. 61/055,258, filed on May 22, 2008.

(51) Int. Cl.
*A61M 16/00* (2006.01)
(52) U.S. Cl. .............................. 128/207.14; 128/207.16
(58) Field of Classification Search .......... 128/207.14–207.16, 204.18, 203.12
See application file for complete search history.

(56) References Cited

U.S. PATENT DOCUMENTS

| | | | | |
|---|---|---|---|---|
| 3,262,447 A | * | 7/1966 | Burke | 128/207.16 |
| 3,683,931 A | * | 8/1972 | Chelucci et al. | 128/207.16 |
| 3,693,624 A | * | 9/1972 | Shiley et al. | 128/207.15 |
| 4,064,882 A | * | 12/1977 | Johnson et al. | 128/207.15 |
| 4,280,492 A | * | 7/1981 | Latham | 128/207.15 |
| 4,569,344 A | * | 2/1986 | Palmer | 128/207.16 |
| 4,759,356 A | | 7/1988 | Muir | |
| 4,805,611 A | * | 2/1989 | Hodgkins | 128/207.14 |
| 5,107,829 A | | 4/1992 | Lambert | |
| 5,233,979 A | * | 8/1993 | Strickland | 128/207.14 |
| 5,303,699 A | | 4/1994 | Bonassa et al. | |
| 5,443,060 A | | 8/1995 | Visveshwara et al. | |
| 5,676,132 A | * | 10/1997 | Tillotson et al. | 128/204.23 |
| 5,765,559 A | | 6/1998 | Kim | |
| 6,484,724 B1 | * | 11/2002 | Sloan | 128/207.17 |
| 6,655,382 B1 | | 12/2003 | Kolobow | |
| 7,328,701 B2 | | 2/2008 | Green | |
| 7,487,778 B2 | * | 2/2009 | Freitag | 128/207.14 |
| 2004/0123868 A1 | * | 7/2004 | Rutter | 128/207.14 |
| 2007/0062540 A1 | * | 3/2007 | Murray-Harris | 128/207.29 |
| 2007/0125387 A1 | | 6/2007 | Zollinger et al. | |

OTHER PUBLICATIONS

Fitsimones, "Tracheostomy and Ventilator Spealing Valves Benefits Beyond Speech", Vital Signs, Apr. 1, 2003. pp. 6-8.

* cited by examiner

*Primary Examiner* — Allana Lewin
(74) *Attorney, Agent, or Firm* — Berenato & White, LLC

(57) ABSTRACT

The invention relates to an infant tracheal device used with a source of air that provides transmission of continuous positive pressure into the lungs of an infant breathing spontaneously using a single tube inspiratory line. The invention serves as an interface with an open trachea. A one-way air valve placed within the tube will not allow pressure to return through the inspiratory line. The internal pressure within the line is measured with a monitor line which is connected to the source and the tracheal device as the pressure enters the infant lungs via a cuffless tracheal tube. A minimal amount of pressure will now be necessary to keep the lungs open. Voluntary exhalation occurs as the pressure of the exhaled air exiting the lungs goes around both the cuffless tracheal tube and out through the nose and mouth of the infant. A pressure release port located on the tracheal device facilitates monitoring and emergency pressure release as necessary. A dispenser port allows use of medication.

4 Claims, 3 Drawing Sheets

INFANT POSITIVE PRESSURE TRACHEAL DEVICE

This application claims the benefit of U.S. provisional application No. 61/055,258, filed May 22, 2008.

BACKGROUND OF THE INVENTION

1. Field of the Invention

The invention relates to the field of infant breathing assistance devices and methods. More specifically, the invention relates to an infant breathing assistance device used in combination with a cuffless tracheal device.

2. Background

Currently there are a number of solutions for applying positive pressure breathing air for infants with apnea hypoxia and generally increased work/effort associated with breathing. Some of these solutions attempt to use conventional machines and methods such as continuous positive airway pressure therapy. But these solutions fail to meet the demand for infants with special needs that have a tracheotomy. Continuous positive airway pressure therapy is limited to nasal or mask therapy. This special requirement makes the infant destined for conventional mechanical ventilators.

The infant tracheal device of the present invention provides a tool which when used will reduce the need for such a cumbersome mechanical machine. Because of the small size, easy access, and comfort—the simple structure allows mobility and safe connectability and is especially adapted for infants.

SUMMARY OF THE INVENTION

The present invention is a positive pressure infant tracheal device which is made up of the following components: a molded tracheal connector interface, a primary pressure release port, a pressure monitor port, a dispenser port, a one-way valve, a smooth walled tubing, a universal connector, a shorter size tracheal connector and/or a longer size tracheal connector. These components are related as follows: the positive pressure tracheal device connects and contains a continuous transmission of positive pressure air into the lungs of a spontaneously breathing infant.

The present invention also provides a method associated with the infant tracheal device which includes the following steps: selecting a tracheal adapter created to interface with the cuffless tracheal device already on the patient, the adapter including a pressure release port placed on the proximal end of the molded tracheal interface; placing a pressure monitor in position vertically on the molded tracheal connector; selecting a length of tubing including an internal one-way valve placed distal to the tracheal connector; and, thereafter connecting the length of tubing to a universal connector to an air supply source. (Either a shorter size tracheal connector, or a longer size tracheal connector, are interchangeable.) As air flows from the source it goes through the tubing into the one way valve which will not allow exhaled air to return into the tubing. Positive pressure air supplied by an air source flows through the molded tracheal interface into the trachea inflating the lungs and, thereafter, normally exhaling out of the nose and mouth. A cuffless tracheal tube is mandatory when using this positive pressure tracheal device because it facilitates spontaneous exhalation through the nose and mouth. Most commonly used infant tracheal tubes are cuffless.

The present invention may also have one or more of the following: a shorter tracheal connector which will reduce dead space. This dead space is associated with the time it takes the pressurized air to reach the lungs. A longer tracheal connector will increase dead space and, accordingly, the time it takes the pressurized air to reach the lungs. The length of the tracheal connector will effect the $O_2/CO_2$ absorption/elimination in relationship to the flow applied. In addition, the smooth walled tubing can be of various lengths and sizes. The smooth walled tubing facilitates maneuverability.

In its most complete version the present invention is made of the following components: a tracheal connector, a pressure release port, a pressure monitor port, a dispenser port, a one-way valve, a smooth walled tubing, a universal connector, a shorter size tracheal connector, a longer size tracheal connector. These components are related such that the positive pressure tracheal device contains and delivers a continuous transmission of positive pressure into the lungs of a spontaneously breathing infant.

The present invention is unique when compared with other known devices and solutions because the small size, easy access, and comfort make it feasible. The simple structure allows mobility and safe connectability. This is the only device specifically for infants that have an open tracheotomy, nasal deformities, facial malformation and periods of apnea. The infant tracheal device provides the care practitioner another tool other than available mechanical ventilation which can be expensive and cumbersome. Similarly, the associated method is unique in that the simple design has the ability to utilize any of the following sources of breathable air: wall $O_2$/air/Oxygen Concentrators/$O_2$ cylinders. This infant tracheal device promotes the use of environmentally safe conditions.

The present invention is also unique in that it is structurally different from other known devices or solutions. More specifically the present invention is unique due to the presence of a one-way valve placed either inside (within) or outside (beyond the end, in a separate connector) a single inspiratory line which transmits positive pressure into the lungs and facilitates an anatomical release of the positive pressure out of the nose and mouth of the infant. Furthermore, the infant positive pressure device promotes removal and elimination of secretions.

The present invention device may also have one or more specific applications associated with its use, for example, in transporting infants. Because of the small size, easy access, comfort and mobility this device is perfect for this task. Similarly, the associated method can be adjusted for home use because the various sources needed to transmit positive pressure into the lungs are not stationary, e.g. $O_2$ cylinders and $O_2$ concentrators. This device is a needed tool in today's highly mobile environment It would be desirable to have a device which, when applied, will improve oxygenation and decrease the work associated with breathing. Furthermore it is desirable to have a device which is environmentally safe. The tracheal device utilizes air coming from any feasible source. Still further this device is cost efficient. The parts are fairly cheap and easy to assemble. There is a need in the medical industry to have this tool to improve the lives of many infants with early lung complications. This tracheal device, the first of its kind, will inflate the lungs and allow passive exhalation which will be through the nose and mouth of the infant and, thusly, facilitate removal of secretions in the more physiologic way of ordinary breathing and should reduce early infant mortality.

DETAILED DESCRIPTION OF THE INVENTION

Figure 1:
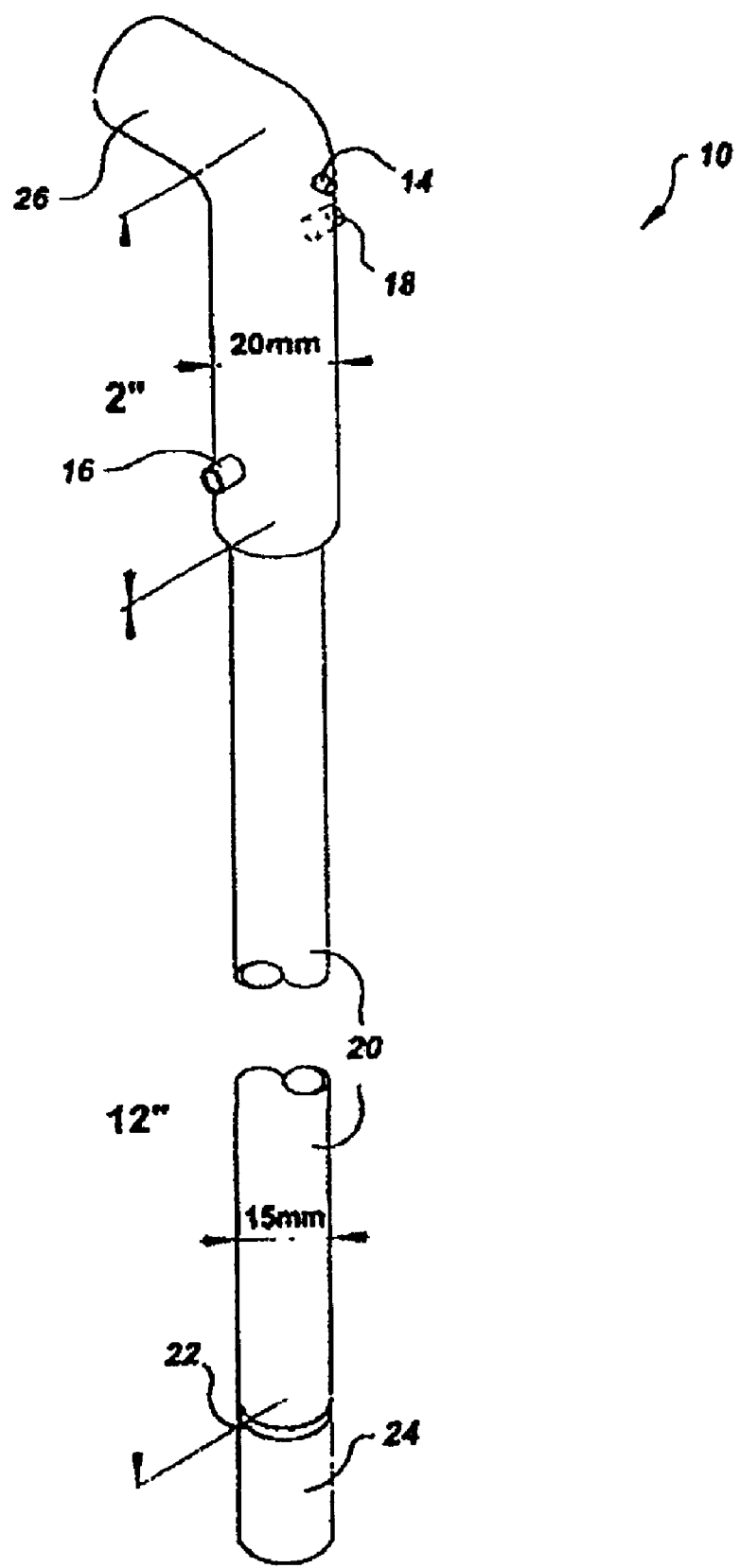
FIG. 1 is a perspective view of the tracheal CPAP Adapter of the invention showing a curved end tracheal adapter.

With respect to FIG. 1: As air flow is generated from a source the gas follows the path of least resistance. The flow is controlled through 20, a (15 mm) 0.787 in bore smooth-walled silicon intersurgical tubing 12" long, connected to 22, a one-way valve (external shell) made of plastic or metal that includes a flexing (neoprene) rubber diaphragm positioned within the air pathway to create a normally closed valve in the air flow pathway. Pressure on the upstream side must be greater than the pressure on the downstream side by a certain amount, known as the pressure differential, for the one-way valve to open allowing flow to proceed. Once positive pressure stops, the diaphragm automatically flexes back to its original closed position. The breathable gas enters the tracheal adapter 26, a 2" long LSG (PolyEtherEtherKetone) (20 mm) 0.787 in hard molded plastic, displaying a curved end. The pressure release port 14 is placed proximal on the hard molded tracheal adapter ensuring overall safety of the subject and facilitates emergency pressure release of invention 10. The pressure monitor port 16, positioned vertically on the hard molded tracheal adapter 26, is provided so that the pressure characteristics will constantly be monitored via an external pressure monitoring device. The dispenser port 18, positioned laterally on the hard molded tracheal adapter, provides easy administration of medications. The universal connector 24 is a simple connector which will facilitate access to numerous sources of different gases to pass through invention 10.

Figure 2:
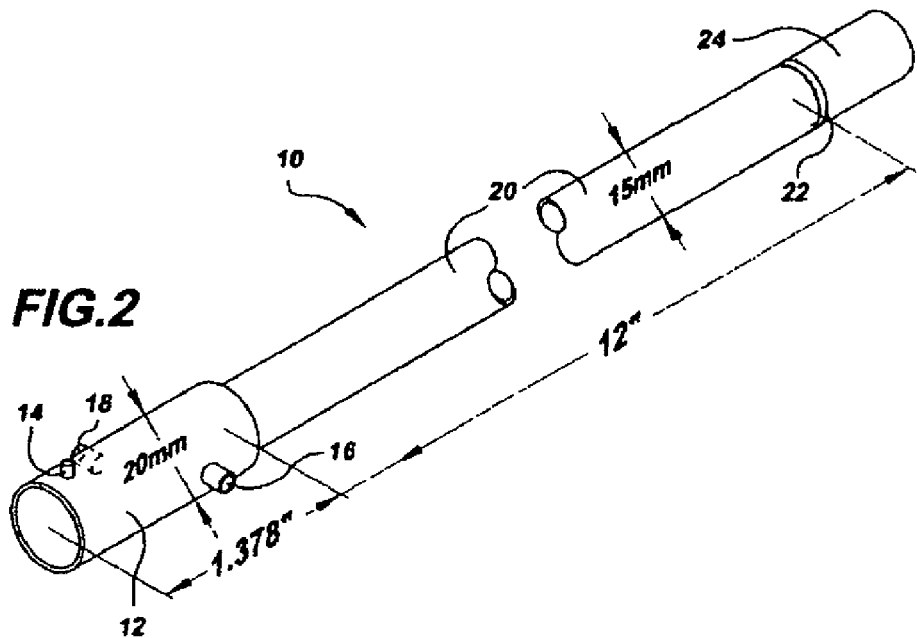
FIG. 2 is another perspective view of an alternate embodiment of the invention showing a straight end tracheal adapter.
Figure 3:
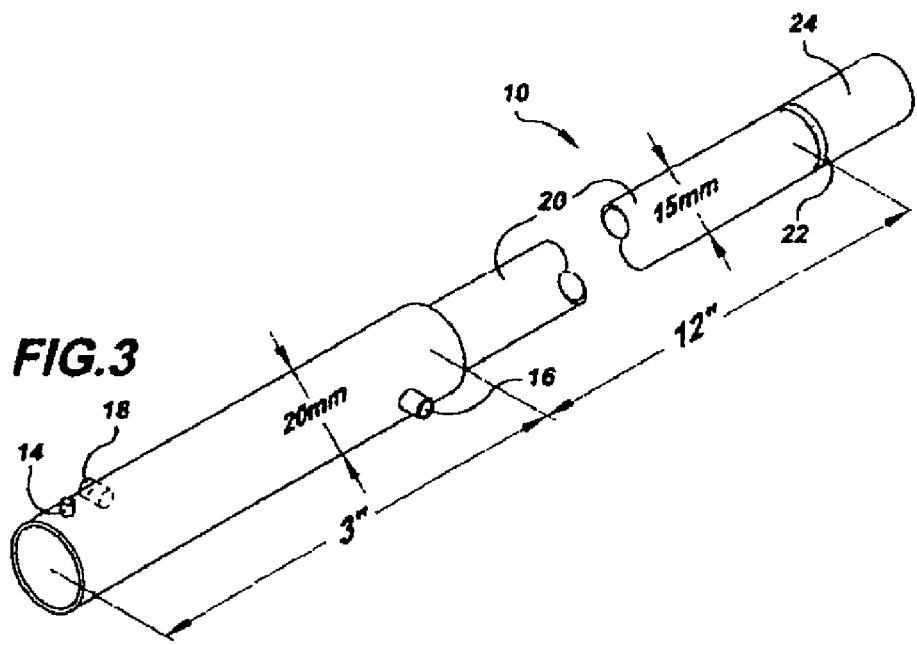
FIG. 3 is another alternative embodiment of the present invention showing a large size tracheal adapter.

With respect to FIGS. 2 and 3: As flow is generated from a source, the gas follows the path of least resistance through 10. The flow is controlled by applying 20, a (15 mm) 0.590 in bore smooth-walled silicon intersurgical tubing 12" long, connected to 22 a one-way valve (external shell) made of plastic or metal a flexing (neoprene) rubber diaphragm positioned within to create a normally closed valve. Pressure on the upstream side must be greater than the pressure on the downstream side known as the pressure differential for the one-way valve to open allowing flow. Once the positive pressure stops, the diaphragm automatically flexes back to its original closed position. The gas enters the tracheal adapter 12, an LSG (PolyEtherEtherKetone) hard molded plastic 1.378" (FIG. 2) or 3.0" (FIG. 3)/0.787 in (20 mm) tracheal adapter. The pressure release port 14, placed proximal on the hard molded tracheal adapter, ensures overall safety of the subject and will facilitate emergency pressure release of the invention 10 as necessary. The pressure monitor port 16 is positioned vertically on the hard molded tracheal adapter 12. The pressure characteristics will constantly be monitored via an external pressure monitoring device. The dispenser port 18 is positioned laterally on the hard molded tracheal adapter and provides easy administration of medication. The universal connector 24 is a simple connector which will facilitate access to numerous sources of different gases to generate sufficient air supply through invention 10.

Figure 4:
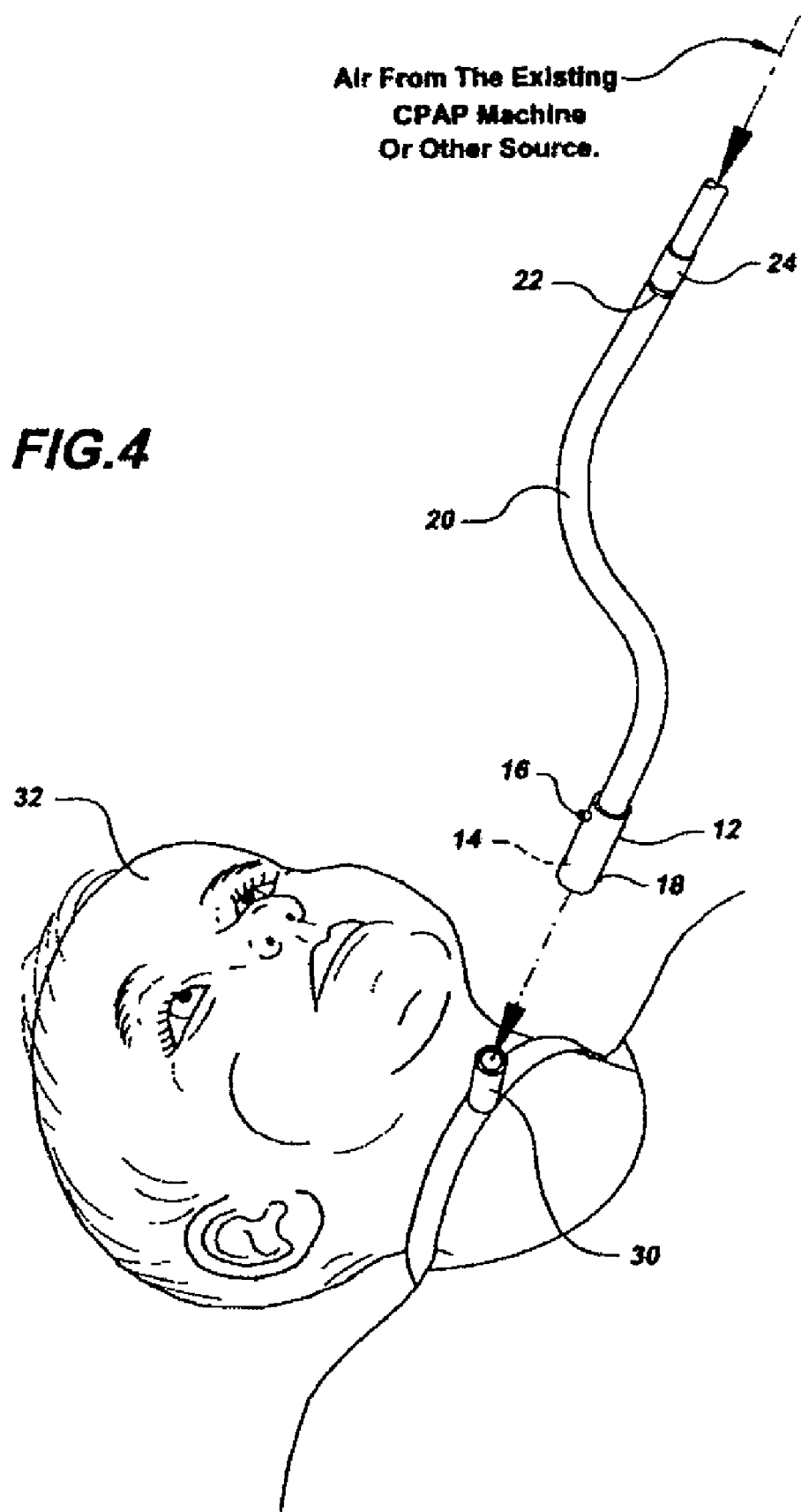
FIG. 4 is a perspective view of the present invention in use.

FIG. 4 shows the device in use on an infant 32 already wearing a cuff-less tracheal device 30. The molded adapter 18 connected to length of tubing 20 enables rapid comfortable connection of a breathable air source to an infant. The configuration of the device 10, including the one way valve 22, enables assisted inhalation while relying on normal positive lung generated pressure exhalation around the cuff-less tracheal device 30 and through the infant's nose and mouth. The various shapes (curved or straight) and lengths of adapters and associated tubes 20 enable selection of a relatively idealized breathing apparatus. The one-way valve 22 may be distal or proximal to the adapter 18 in the tubing 20 or may be incorporated into the adapter 18 itself. The more proximal the valve location, the less dead space is provided for assisted inhalation. In some instances, greater dead space may be desired and would require one-way valve placement more distal from the adapter.

The infant positive pressure device described herein can be of various sizes/length/width as necessary to provide a broad spectrum of applications and specific requirements. In addition, the one-way valve can be of various sizes and shapes and types, i.e., check valve, clack valve, non-return valve, ball check valve, diaphragm check valve, swing check valve, clapper valve, stop-check valve, lift-check valve. Basically, any check valve used inside or outside of the tube or tubings herein which, when connected in series therewith, will allow/ prohibit flow of gas or fluid, appropriately, into a cuffless tracheal tube resulting in the inflation of the lungs and provide for normal exhalation through the path of least resistance (i.e., around the device and out through the nose and mouth).

Pressure monitor alarm systems connect to the pressure port and generate an alarm signal either when the maximum pressure during inspiration varies or when mean pressure during inspiration varies. Continuous airway pressure monitoring is a simple non-invasive technique for displaying a patient's real-time pressure waveform on bedside monitoring systems. Positive waveform deflections indicate positive pressure ventilations and negative deflections that indicate spontaneous inspiratory efforts. The components of continuous airway pressure monitoring are well known in the art to clinicians. A clinician chooses a channel on the bedside monitor (any known system for such purpose may be used), a transducer cable (i.e., a high-pressure tubing with a transducer), such as that used for pulmonary artery and arterial pressure monitoring; assemble the tubing and connect to the transducer; connect the distal end of the tubing to the proximal tracheal adapter attachment. This technique would be used in critical care environments. Home care (stand alone) pressure alarms can be connected to the tracheal connector using one air-line. This basic monitoring system (low-pressure) device is capable of detecting a disconnection of the breathing system. Low-pressure monitoring devices are designed to annunciate an alarm if the breathing system pressure fails to exceed a minimum threshold pressure within a fixed time. The high-pressure alarm is important in the detection of hazardous situation that can lead to pulmonary barotraumas. Remote alarms system can be incorporated, as necessary, with the tracheal device. Flow protection is generally sized for use in situations where significant quantities of breathable gas or fluid must be quickly discharged in order to protect the integrity of the patient. The tracheal device allows venting through the nose and mouth of the patient with the use of a cuffless tube. The pressure release port is another safety component incorporated into the tracheal device to insure patient care.

While the present invention has been described above in terms of specific embodiments, it is to be understood that the invention is not limited to these disclosed embodiments. Many modifications and other embodiments of the invention will come to mind of those skilled in the art to which this invention pertains, and which are intended to be and are covered by both this disclosure and the appended claims. It is indeed intended that the scope of the invention should be determined by proper interpretation and construction of the appended claims and their legal equivalents, as understood by those of skill in the art relying upon the disclosure in this specification and the attached drawings.

The invention claimed is:

1. An infant positive pressure breathing apparatus, comprising:
   a source of breathable inspiratory air connected, in series, to a first length of smooth walled intersurgical soft flexible tubing and a one way valve, said one way valve limiting the flow of said air through the first length of said tubing except when a pressure of said air source exceeds the pressure of air in the flexible tubing at a location beyond the one-way valve, said one way valve connected in-turn via a second length of smooth walled flexible tubing not exceeding about 12 inches in overall length to a molded tracheal connector interface not exceeding about 2-3 inches in overall dimension for connecting to an open patient associated cuff-less tracheal device, said molded tracheal connector interface including a primary pressure release port located proximally on said molded tracheal interface with respect to its connection to said cuff-less tracheal device, a pressure monitor port located distally with respect to said molded tracheal connector interface connection to said cuff-less tracheal device, and a medication dispenser port located laterally with respect to said primary pressure release port,
   wherein when said inspiratory air source is actively supplying air, the associated infant patient may inhale relying on assistance provided from said air source and exhale normally using lung generated positive pressure and pass exhaled air around and past said cuff-less tracheal device and out said patient's nose and mouth.

2. An apparatus as in claim 1, wherein: said molded tracheal interface is curved along its length as it connects from said second length of tubing to said cuff-less tracheal device.

3. An apparatus as in claim 1, wherein: said one way valve is located distally in said second length of tubing with respect to said molded tracheal interface.

4. An apparatus as in claim 1, wherein: said one way valve is located proximally in said second length of tubing with respect to said molded tracheal interface.

* * * * *